(12) United States Patent
Kim et al.

(10) Patent No.: US 9,675,298 B2
(45) Date of Patent: Jun. 13, 2017

(54) APPARATUS AND METHOD FOR MEASURING BIOELECTRIC SIGNALS

(75) Inventors: Jong-pal Kim, Seoul (KR); Byung-hoon Ko, Hwaseong-si (KR); Tak-hyung Lee, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 862 days.

(21) Appl. No.: 13/592,639

(22) Filed: Aug. 23, 2012

(65) Prior Publication Data

US 2013/0053675 A1 Feb. 28, 2013

(30) Foreign Application Priority Data

Aug. 25, 2011 (KR) .................. 10-2011-0085148

(51) Int. Cl.
*A61B 5/04* (2006.01)
*A61B 5/00* (2006.01)
(Continued)

(52) U.S. Cl.
CPC ............ *A61B 5/7214* (2013.01); *A61B 5/04* (2013.01); *A61B 5/0488* (2013.01);
(Continued)

(58) Field of Classification Search
CPC ....... A61B 5/04; A61B 5/0488; A61B 5/0478; A61B 5/04284; A61B 5/0428; A61B 5/04058; A61B 5/0408; A61B 5/0402; A61B 5/04004; A61B 5/7207; A61B 5/7203; A61B 5/6832–5/6833;
(Continued)

(56) References Cited

U.S. PATENT DOCUMENTS

| 4,004,578 A | 1/1977 | Palmius |
| 4,969,468 A | 11/1990 | Byers et al. |

(Continued)

FOREIGN PATENT DOCUMENTS

| JP | 09-508293 A | 8/1997 |
| JP | 2008-536605 A | 9/2008 |

(Continued)

OTHER PUBLICATIONS

Extended European Search Report issued Jan. 25, 2013 in counterpart European Application No. 12181656.5-1265; (12 pages, in English).

(Continued)

*Primary Examiner* — Lee S Cohen
*Assistant Examiner* — Erin M Cardinal
(74) *Attorney, Agent, or Firm* — NSIP Law

(57) ABSTRACT

A bioelectric signal measurement apparatus includes a first interface configured to detect a bioelectric signal of a testee through electrical interfacing with a skin of the testee; a second interface configured to detect a signal different from the bioelectric signal through electrical interfacing with the skin, the second interface electrically interfacing with the skin in a state that is different from a state in which the first interface electrically interfaces with the skin; and a signal processor configured to remove, from the detected bioelectric signal, a motion artifact between the first interface and the skin using the detected signal different from the bioelectric signal.

17 Claims, 8 Drawing Sheets

(51) Int. Cl.
*A61B 5/0488* (2006.01)
*A61B 5/053* (2006.01)

(52) U.S. Cl.
CPC ............ *A61B 5/7228* (2013.01); *A61B 5/053* (2013.01); *A61B 5/6832* (2013.01); *A61B 5/721* (2013.01); *A61B 5/7207* (2013.01)

(58) Field of Classification Search
CPC ... A61B 5/6801; A61B 5/0531; A61B 5/7228; A61B 5/7214; A61B 5/721; A61B 2562/0214; A61B 2562/06–2562/066; A61B 2560/0412
USPC ....... 600/382, 372, 301, 547, 546, 544–545, 600/509, 393, 391–392
See application file for complete search history.

(56) References Cited

U.S. PATENT DOCUMENTS

| | | | | |
|---|---|---|---|---|
| 5,206,602 | A * | 4/1993 | Baumgartner | A61B 5/04004 330/258 |
| 5,704,365 | A * | 1/1998 | Albrecht | A61B 5/0408 128/901 |
| 5,749,369 | A * | 5/1998 | Rabinovich | A61B 5/0535 600/372 |
| 5,921,939 | A * | 7/1999 | Danielsson | A61B 5/0424 600/509 |
| 6,807,438 | B1 * | 10/2004 | Brun Del Re et al. | 600/372 |
| 6,961,601 | B2 * | 11/2005 | Matthews et al. | 600/372 |
| 7,711,414 | B2 | 5/2010 | Shin et al. | |
| 2002/0028991 | A1 * | 3/2002 | Thompson | 600/372 |
| 2002/0038092 | A1 * | 3/2002 | Stanaland et al. | 600/509 |
| 2004/0073104 | A1 * | 4/2004 | Brun del Re et al. | 600/372 |
| 2006/0015033 | A1 * | 1/2006 | Blakley | A61B 5/0428 600/509 |
| 2007/0135701 | A1 * | 6/2007 | Fridman | A61B 5/0408 600/382 |
| 2008/0208028 | A1 | 8/2008 | Thijs et al. | |
| 2010/0004517 | A1 | 1/2010 | Bryenton et al. | |
| 2010/0331659 | A1 | 12/2010 | Sheraton, Sr. et al. | |
| 2011/0105874 | A1 * | 5/2011 | Feddes | A61B 5/04 600/372 |
| 2012/0116198 | A1 * | 5/2012 | Veen et al. | 600/372 |

FOREIGN PATENT DOCUMENTS

| | | |
|---|---|---|
| KR | 10-0321261 B1 | 1/2002 |
| KR | 10-2005-0072965 A | 7/2005 |
| KR | 10-0659511 B1 | 12/2006 |
| KR | 10-0866547 B1 | 11/2008 |
| KR | 10-0879787 B1 | 1/2009 |
| KR | 10-2010-0061824 A | 6/2010 |
| WO | WO 2011/007292 A1 | 1/2011 |

OTHER PUBLICATIONS

Chinese Office Action issued on Jul. 1, 2015 in counterpart Chinese Application No. 201210304313.7 (15 pages with English translation).

Japanese Patent Office issued on Aug. 9, 2016 in counterpart Japanese Application No. 2012-187001 (9 pages with English translation).

* cited by examiner

[RELATED ART]

APPARATUS AND METHOD FOR MEASURING BIOELECTRIC SIGNALS

CROSS-REFERENCE TO RELATED APPLICATIONS

This application claims the benefit of Korean Patent Application No. 10-2011-0085148 filed on Aug. 25, 2011, in the Korean Intellectual Property Office, the disclosure of which is incorporated herein by reference in its entirety for all purposes.

BACKGROUND

1. Field

This disclosure relates to methods and apparatuses for measuring bioelectric signals of a testee more accurately by removing a motion artifact from the bioelectric signals.

2. Description of Related Art

A variety of medical equipment to diagnose a patient's state of health have been developed. Medical equipment that measures bioelectric signals of a patient have become increasingly important in consideration of convenience of a patient during a health diagnosis process and speed in producing a health diagnosis result.

Bioelectric signals are signals in the form of an electric potential or an electric current that are generated by muscle cells or nerve cells of a testee, and are obtained by analyzing changes in an electric signal detected by electrodes attached to the body of the testee. When the bioelectric signals are measured, a motion artifact is generated in the bioelectric signals due to movement of the testee. The motion artifact interferes with accurate measurement of bioelectric signals by distorting a waveform of a measurement result.

SUMMARY

In one general aspect, a bioelectric signal measurement apparatus includes a first interface configured to detect a bioelectric signal of a testee through electrical interfacing with a skin of the testee; a second interface configured to detect a signal different from the bioelectric signal through electrical interfacing with the skin, the second interface electrically interfacing with the skin in a state that is different from a state in which the first interface electrically interfaces with the skin; and a signal processor configured to remove, from the detected bioelectric signal, a motion artifact between the first interface and the skin using the detected signal different from the bioelectric signal.

An impedance of the second interface due to the electrical interfacing with the skin may be larger than an impedance of the first interface due to the electrical interfacing with the skin.

The first interface may be further configured to electrically interface with the skin through a predetermined material, and the second interface may be further configured electrically interface directly with the skin, causing the impedance of the second interface to be larger than the impedance of the first interface.

The first interface may include at least one electrode including a sharp protrusion configured to penetrate a stratum corneum of the skin, and the second interface may include at least one electrode including a flat plate configured to contact a surface of the skin.

The bioelectric signal measurement apparatus of claim 1, wherein the first interface may include a plurality of electrodes arranged on a substrate formed of an insulating material; and the second interface may include a plurality of electrodes alternately arranged with the electrodes of the first interface on the substrate so that each of the electrodes of the second interface is disposed within a critical distance from at least one of the electrodes of the first interface.

The bioelectric signal measurement apparatus of claim 1, wherein the first interface may include a single electrode; and the second interface may include a plurality of electrodes surrounding the single electrode of the first interface so that each of the electrodes of the second interface is disposed within a critical distance from the single electrode of the first interface.

The bioelectric signal measurement apparatus of claim 1, wherein the first interface may include at least one wet electrode; and the second interface may include at least one dry electrode.

The bioelectric signal measurement apparatus of claim 1, wherein the signal processor may include a motion artifact extraction unit configured to extract a signal proportional to the motion artifact using the signal detected by the second interface; and a bioelectric signal extraction unit configured to remove the motion artifact from the detected bioelectric signal using the signal proportional to the motion artifact.

The bioelectric signal measurement apparatus may further include a third interface configured to detect the bioelectric signal through electrical interfacing with the skin, the third interface being separated from the first interface by a predetermined distance; and a fourth interface configured to detect the signal different from the bioelectric signal through electrical interfacing with the skin, the fourth interface electrically interfacing with the skin in the state that is different from the state in which the first interface electrically interfaces with the skin. The second interface may be disposed within a critical distance from the first interface; the fourth interface is disposed within the critical distance from the third interface. The signal detected by the second interface and the fourth interface may be an electric potential signal. The motion artifact extraction unit may be further configured to extract the signal proportional to the motion artifact by differentially amplifying electric potential values of the electric potential signal detected by the second interface and the fourth interface.

The motion artifact extraction unit may be further configured to apply a predetermined current modulated at a predetermined frequency to the skin through the second interface and the fourth interface to produce the electric potential values of the electric potential signal; differentially amplify the electric potential values of the electric potential signal to produce an amplified signal; and demodulate the amplified signal to extract the signal proportional to the motion artifact.

The bioelectric signal extraction unit may be further configured to extract a bioelectric signal including the motion artifact by differentially amplifying electric potential values of the bioelectric signal detected by the first interface and the third interface; and remove the signal proportional to the motion artifact from the bioelectric signal including the motion artifact to obtain a bioelectric signal free of the motion artifact.

The bioelectric signal extraction unit may be further configured to adaptively filter the signal proportional to the motion artifact to obtain an estimated motion artifact signal; and remove the estimated motion signal from the detected bioelectric signal to obtain a bioelectric signal free of the motion artifact.

In another general aspect, a method of measuring a bioelectric signal includes receiving a bioelectric signal detected by a first interface and a third interface each electrically interfacing with a skin of a testee; receiving an electric potential signal detected by a second interface and a fourth interface each electrically interfacing with the skin in a state that is different from a state in which the first interface and the third interface electrically interface with the skin; obtaining a signal proportional to a motion artifact using the electric potential signal; and removing the motion artifact from the bioelectric signal using the signal proportional to the motion artifact.

The first interface, the second interface, the third interface, and the fourth interface may each include a plurality of electrodes; the electrodes of the first interface may be alternately arranged with the electrodes of the second interface so that each of the electrodes of the second interface is disposed within a critical distance from at least one of the electrodes of the first interface; the electrodes of the third interface may be alternately arranged with the electrodes of the fourth interface so that each of the electrodes of the fourth interface is disposed within a critical distance of at least one of the electrodes of the third interface; and the electrodes of the third interface may be disposed a predetermined distance from the electrodes of the first interface.

The first interface and the third interface may each include at least one wet electrode; and the second interface and the fourth interface may each include at least one dry electrode.

In another general aspect, a non-transitory computer-readable storage medium stores a program for controlling a computer to perform the method described above.

In another general aspect, a bioelectric signal measurement apparatus includes a first interface configured to detect a first signal from a skin of a testee, the detected first signal detected by the first interface being distorted by movement between the first interface and the skin; a second interface configured to detect a second signal from the skin, the detected second signal detected by the second interface being distorted by movement between the second interface and the skin, a distortion of the detected second signal detected by the second interface being greater than a distortion of the detected first signal detected by the first interface; and a signal processor configured to obtain a signal free of distortion due to the movement between the first interface and the skin from the detected first signal detected by the first interface using the detected second signal detected by the second interface.

A contact impedance between the second interface and the skin may be larger than a contact impedance between the first interface and the skin, causing the distortion of the detected second signal detected by the second interface to be greater than the distortion of the detected first signal detected by the first interface.

The first interface may include at least one electrode including a sharp protrusion configured to penetrate a stratum corneum of the skin; and the second interface may include at least one electrode including a flat plate configured to contact a surface of the skin.

The second interface may be disposed within a critical distance from the first interface so that the distortion of the detected second signal detected by the second interface has substantially a same shape as the distortion of the detected first signal detected by the first interface.

Other features and aspects will be apparent from the following detailed description, the drawings, and the claims.

BRIEF DESCRIPTION OF THE DRAWINGS

The above and other aspects will become apparent and more readily appreciated from the following description, taken in conjunction with the accompanying drawings in which.

DETAILED DESCRIPTION

Figure 1:
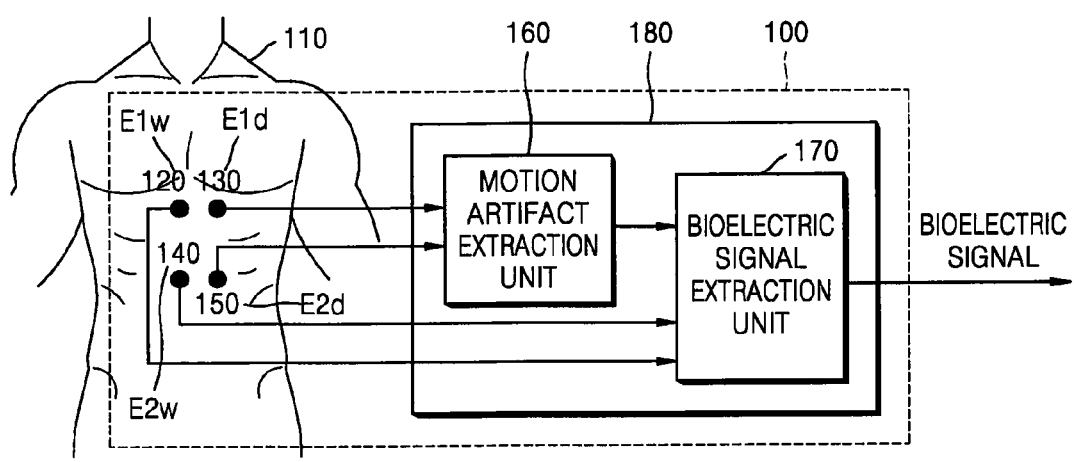
FIG. 1 schematically illustrates an example of a structure of a bioelectric signal measurement apparatus.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 schematically illustrates an example of a structure of a bioelectric signal measurement apparatus 100. Referring to FIG. 1, the bioelectric signal measurement apparatus 100 includes interfaces E1w (120), E1d (130), E2w (140), and E2d (150), a motion artifact extraction unit 160, and a bioelectric signal extraction unit 170. The motion artifact extraction unit 160 and the bioelectric signal extraction unit 170 constitute a signal processor 180. The bioelectric signal measurement apparatus 100 of FIG. 1 is a merely one example, and various modifications based on the constituent elements illustrated in FIG. 1 will be apparent to one of ordinary skill in the art to which the present description pertains.

The bioelectric signal measurement apparatus 100 is used to measure bioelectric signals of a testee 110. Bioelectric signals are signals in the form of an electric potential or an electric current that are generated by muscle cells or nerve cells of a human body, and may be referred to as bioelectric potentials or bioelectric currents. For convenience of explanation, it will be assumed that the bioelectric signals detected using the bioelectric signal measurement apparatus 100 are in the form of an electric potential.

Referring to FIG. 1, the bioelectric signal measurement apparatus 100 detects bioelectric signals using the interfaces E1w (120), E1d (130), E2w (140), and E2d (150) attached to the body of the testee 110. The interfaces E1w (120), E1d (130), E2w (140), and E2d (150) are electrically connected to i.e., electrically interface with, the skin of the testee 110 to detect bioelectric signals of the testee 110. That is, the interfaces E1w (120), E1d (130), E2w (140), and E2d (150) are electrodes that electrically contact a living body and output electric signals from the living body to a circuit for measuring bioelectric signals. Each of the interfaces E1w (120), E1d (130), E2w (140), and E2d (150) includes one or more electrodes. If an interface has more than one electrode, the electrodes are connected together at a node so that all of the electrodes of the interface have the same electric potential. The one or more electrodes of the interface are arranged in various ways for accurate detection of a bioelectric signal, and contact the skin of the testee 110 either directly, or indirectly via a predetermined material, as will be described below. The arrangement of the electrodes of the interfaces E1w (120), E1d (130), E2w (140), and E2d (150) will be described below with reference to FIGS. 4, 5, 7A, and 7B.

In general, a bioelectric signal is measured by detecting a difference between electric potential values, that is, voltages, detected by two interfaces E1w (120) and E2w (140) having different electric potentials at positions separated from each other by a predetermined distance. In greater detail, a bioelectric signal is measured by differentially amplifying electric potential values acquired from the two interfaces E1w (120) and E2w (140) attached at positions separated from each other by the predetermined distance on the skin of the testee 110 to obtain a waveform of a voltage value corresponding to the bioelectric signal. The waveform of the voltage value of the measured bioelectric signal includes noise.

The bioelectric signal corresponding to an electric potential or an electric current generated in nerve cells or muscle cells is an electric signal having a very small amplitude, and thus is greatly affected by noise. In particular, the bioelectric signal measurement apparatus 100 measures bioelectric signal using the electrodes of the interfaces E1w (120) and E2w (140) attached to a human body, so the bioelectric signal including noise that is measured is influenced by movement of the body during the measurement of the bioelectric signal through the attached electrodes. The noise due to the movement of the body is referred to as a motion artifact, and deteriorates accuracy of the measured bioelectric signal so that accurate recognition of an actual state of the testee 110 and diagnosis and treatment of a disease are made difficult.

In greater detail, the motion artifact is due to a variation in an electrode-skin contact impedance (hereinafter referred to as a contact impedance) between the skin and the electrode due to the movement of the body. Such a contact impedance variation generates noise the measured bioelectric signal. The motion artifact distorts the waveform of the measured bioelectric signal, and therefore the motion artifact due to the movement of the body must be removed from the measured bioelectric signal for accurate measurement of the bioelectric signal.

The motion artifact does not have a constant pattern, and often varies according to the movement of the body. Also, the motion artifact is a signal in a frequency range similar to a frequency range of a bioelectric signal to be measured, and therefore the motion artifact cannot be removed from the measured bioelectric signal by simple filtering. Thus, the bioelectric signal measurement apparatus 100 measures a signal proportional to the motion artifact separate from a bioelectric signal including the motion artifact, and removes the signal from the bioelectric signal including the motion artifact using the signal proportional to the motion artifact, thereby obtaining a bioelectric signal free of the motion artifact.

The motion artifact is generated because the contact impedance variation of the testee 110 due to movement causes a change in the electric potential generated by the electrode, which appears as noise in the measured bioelectric signal. The motion artifact is measured by using the contact impedance variation, which is highly correlated with the motion artifact. That is, the motion artifact affecting a bioelectric signal may be measured by measuring a signal proportional to the contact impedance variation due to movement. The signal proportional to the contact impedance variation due to movement may be measured by flowing a current i0 from the electrode into the body of the testee 110, detecting a change $\Delta v$ in an electric potential produced by the current i0 using the electrodes attached to the body and separated from each other by a predetermined distance, and differentially amplifying the change $\Delta v$ in the electric potentials detected by the electrodes.

Referring to Equation 1 below, the change $\Delta v$ in the electric potential produced by the constant current i0 is proportional to the contact impedance variation. Thus, the motion artifact is measured by making the current i0 flow into the skin and using the change $\Delta v$ of the electric potential detected by the electrodes attached to the skin. The current i0 flowing into the skin of the testee 110 has a frequency fc that does not overlap with the frequency range of a bioelectric signal so that the effect of a bioelectric signal with respect to the measured motion artifact may be reduced. When the current i0 having the frequency fc flows into the skin, the change $\Delta v$ of the detected electric potential is a signal modulated at the frequency fc. Then, the signal modulated at the frequency fc is detected and demodulated to recover the original signal.

$$\Delta z = \frac{\Delta v}{i0} \qquad (1)$$

The change $\Delta v$ of the detected electric potential (hereinafter referred to as electric potential signal $\Delta v$) may be detected by using the interfaces E1d (130) and E2d (150) formed of one or more electrodes attached to the skin of the testee 110 separate from the measurement of a bioelectric signal. That is, the bioelectric signal measurement apparatus 100 measures the bioelectric signal using the two interfaces E1w (120) and E2w (140), and detects the electric potential signal Δv using the two separate interfaces E1d (130) and E2d (150).

Figure 2:
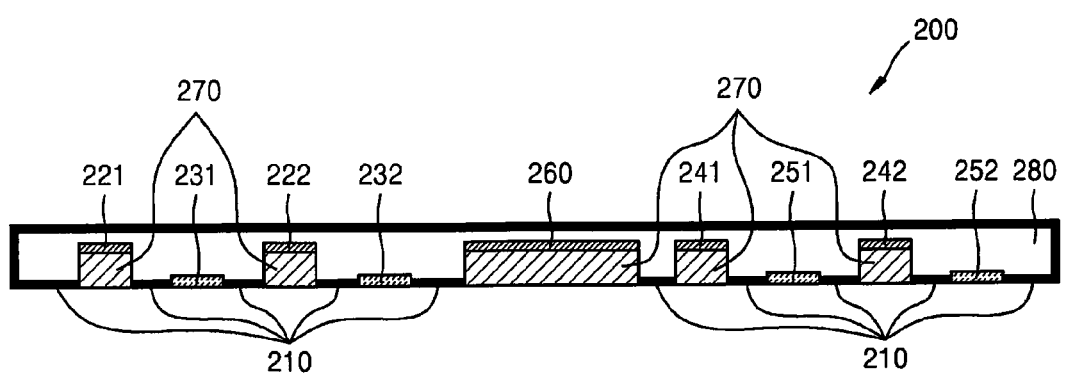
FIG. 2 is a cross-sectional view of an example of a contact surface where the bioelectric signal measurement apparatus of FIG. 1 contacts the skin of a testee.

The electrodes of the interfaces E1w (120) and E2w (140) for detecting the bioelectric signal electrically interface with the skin of the testee 110 using a hydrogel 270 (see FIG. 2). The hydrogel 270 is an electrolyte gel. When an electrode contacts the skin via the hydrogel 270, a contact impedance, which is an electrical resistance between the electrode and the skin, is reduced, compared to a case in which an electrode formed of a conductive metal directly contacts the skin. That is, since the contact impedance between the electrode and the skin is decreased by using the hydrogel 270, the influence of the contact impedance on a bioelectric signal having a small amplitude is reduced, which is advantageous for the measurement of the bioelectric signal. Accordingly, even when the contact impedance changes due to the movement of the testee 110, if an average amount of the contact impedance is small, the influence on the bioelectric signal is small so that the detected bioelectric signal is relatively less affected by the motion artifact. This enables the bioelectric signal measurement apparatus 100 to have an appropriate signal to noise ratio (SNR) for detecting a bioelectric signal. Thus, when the bioelectric signal is detected using the hydrogel 270, the influence of the motion artifact on the bioelectric signal is reduced so that a relatively uniform and stable bioelectric signal may be obtained.

The electrodes of the interfaces E1d (130) and E2d (150) that detect the electric potential signal Δv detect a signal by directly contacting the skin without the hydrogel 270. Thus, the electrodes of the interfaces E1d (130) and E2d (150) that directly contact the skin without the hydrogel 270 have a higher contact impedance than the interfaces E1w (120) and E2w (140) that electrically interface with the skin using the hydrogel 270.

That is, the interfaces E1w (120) and E2w (140) that detect the bioelectric signal electrically interface with the skin in a different state than the interfaces E1d (130) and E2d (150) that detect the electric potential signal Δv, and have different electrical conditions than the interfaces E1d (130) and E2d (150), which means that the interfaces E1d (130) and E2d (150) that detect the electric potential signal Δv have a higher contact impedance than the interfaces E1w (120) and E2w (140) that detect the bioelectric signal.

FIG. 2 is a cross-sectional view of an example of a contact surface where the bioelectric signal measurement apparatus 100 of FIG. 1 contacts the skin of the testee 110. Referring to FIG. 2, electrodes 231 and 232 of the interface E1d (130) and electrodes 251 and 252 of the interface E2d (150) that detect the electric potential signal Δv directly contact the skin of the testee 110 via holes of an adhesive sheet 210. In contrast, electrodes 221 and 222 of the interface E1w (120) and electrodes 241 and 242 of the interface E2w (140) that detect the bioelectric signal contact the skin of the testee 110 via the hydrogel 270, i.e., they do not directly contact the skin of the testee 110, but indirectly contact the skin of the testee 110 via the hydrogel 270. The hydrogel 270, which is an electrolyte gel as described above, electrically interfaces with the skin of the testee 110 and the electrodes 221 and 222 of the interface E1w (120) and the electrodes 241 and 242 of the interface E2w (140) that detect the bioelectric signal.

An electrode made of a conductive metal that electrically interfaces with the skin via the hydrogel 270 is referred to as a wet electrode. An electrode made of a conductive metal that electrically interfaces with the skin via direct contact is referred to as a dry electrode. Typically, a wet electrode is a silver plate coated with silver chloride (AgCl), and a dry electrode is a plate made of gold (Au). However, these are merely examples, and other materials may be used for a wet electrode and a dry electrode as will be apparent to one of ordinary skill in the art.

The interfaces E1d (130) and E2d (150) that detect the electric potential signal Δv use dry electrodes having a high contact impedance. Compared to a wet electrode, a dry electrode has a higher correlation between a change in the contact impedance and a motion artifact. Thus, more accurate measurement of bioelectric signals free of a motion artifact is possible by using dry electrodes in the detection of the electric potential signal Δv.

Figure 3:
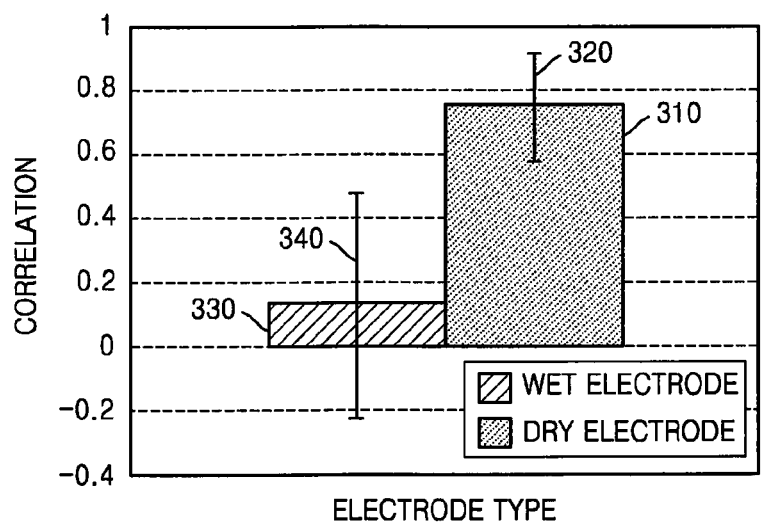
FIG. 3 is a graph showing an example of a correlation between a motion artifact and a change in contact impedance according to the type of electrodes forming interfaces of the bioelectric signal measurement apparatus of FIG. 1.

FIG. 3 is a graph showing an example of a correlation between a motion artifact and a change in contact impedance according to the type of electrodes of interfaces of the bioelectric signal measurement apparatus 100 of FIG. 1. The correlation signifies a degree of correlation between two variables, in this case, between the contact impedance variation and the motion artifact. A large correlation signifies that the degree of correlation between the contact impedance variation and the motion artifact is large. Accordingly, for the electrode having a large correlation, the variation in the contact impedance due to the contact between the electrode and the skin of the testee 110 more accurately reflects the motion artifact included in the bioelectric signal during the measurement of the bioelectric signal.

In the graph of FIG. 3, the x axis denotes the type of an electrode, that is, a wet electrode and a dry electrode, whereas the y axis denotes a correlation between the contact impedance variation and the motion artifact by a correlation coefficient. The correlation coefficient is a value quantitatively indicating a degree of correlation between the contact impedance variation and the motion artifact, and may have a value between −1 to +1. The larger the absolute value of the correlation coefficient is, the higher the correlation is. When the correlation coefficient value is 0, no correlation exists.

An area 310 denotes an average correlation coefficient value of a dry electrode. An area 330 denotes an average correlation coefficient value of a wet electrode. A line 320 denotes a range of a standard deviation of the average correlation coefficient value of a dry electrode. A line 340 denotes a range of a standard deviation of the average correlation coefficient value of a wet electrode.

Referring to the graph of FIG. 3, the average correlation coefficient value (area 330) of a wet electrode is about 0.13, indicating a low correlation between the contact impedance and the motion artifact, while the average correlation coefficient value (area 310) of a dry electrode exhibits a high correlation coefficient value of about 0.75, indicating a high correlation between the contact impedance variation and the motion artifact. Thus, the average correlation coefficient value (area 310) of a dry electrode of 0.75 is about 5.8 times the average correlation coefficient value (area 330) of a wet electrode of 0.13. Considering each of the standard deviation values (line 320 and line 340), the absolute value of the correlation coefficient of a dry electrode is greater than the absolute value of the correlation coefficient of a wet electrode. That is, when a motion artifact is measured by detecting the electric potential signal Δv using a dry electrode, the contact impedance variation accurately reflects the motion artifact so that a more accurate measurement of the motion artifact is possible. The reason the correlation of the dry electrode is relatively high is because the contact impedance of the dry electrode that directly contacts the skin is relatively high compared to the contact impedance of the wet electrode that contacts the skin via the hydrogel 270. This is because the contact impedance variation due to movement appears greater when the measurement is performed using the dry electrode than using the wet electrode. Thus, by measuring the electric potential signal Δv using the dry electrode having a relatively high correlation with the motion artifact, it is possible to detect a more accurate bioelectric signal free of the motion artifact.

Thus, the bioelectric signal measurement apparatus 100 performs measurement using wet electrodes having a relatively low contact impedance that has a relatively low correlation with a motion artifact as the electrodes of the interfaces E1w (120) and E2w (140) for the detecting bioelectric signal, and using dry electrodes having a relatively high contact impedance that has a relatively high correlation with a motion artifact as the electrodes of the interfaces E1d (130) and E2d (150) for measuring the electric potential signal Δv.

Also, in order to measure an accurate bioelectric signal free of a motion artifact, the motion artifact measured using the electrodes of the interfaces E1d (130) and E2d (150) has almost the same shape as the motion artifact included in the bioelectric signal. Thus, the electrodes of the interfaces E1d (130) and E2d (150) for measuring the electric potential signal Δv are disposed within a critical distance from the electrodes of the interfaces E1w (120) and E2w (140) for measuring the bioelectric signal. That is, since the motion artifact is caused by a contact impedance variation due to movement, to detect the motion artifact having almost the same shape as the motion artifact included in the bioelectric signal, the contact impedance variation at the electrodes for measuring the electric potential signal Δv must have almost the same shape as the contact impedance variation at the electrodes for measuring the bioelectric signal. Therefore, the critical distance is a distance that is short enough so that a contact impedance variation due to movement of the testee 110 appears at the electrodes for detecting the electric potential signal Δv has almost the same shape as a contact impedance variation at the electrodes for detecting the bioelectric signal. Referring to FIG. 2, each of the electrodes 231 and 232 of the interface E1d (130) and the electrodes 251 and 252 of the interface E2d (150) for measuring the electric potential signal Δv is separated from at least one of the electrodes 221 and 222 of the interface E1w (120) and the electrodes 241 and 242 of the interface E2w (140) for measuring the bioelectric signal by the critical distance or less.

The detailed structure of the electrodes 231 and 232 of the interface E1d (130) and the electrodes 251 and 252 of the interface E2d (150) for measuring the electric potential signal Δv and the electrodes 221 and 222 of the interface E1w (120) and the electrodes 241 and 242 of the interface E2w (140) for measuring the bioelectric signal are described as follows with reference to FIG. 2. Referring to FIG. 2, the contact surface 200 where the bioelectric signal measurement apparatus 100 of FIG. 1 contacts the skin of the testee 110 includes the adhesive sheet 210, the electrodes 221 and 222 of the interface E1w (120) and the electrodes 241 and 242 of the interface E2w (140) for measuring the bioelectric signal, the electrodes 231 and 232 of the interface E1d (130) and the electrodes 251 and 252 of the interface E2d (150) for measuring the electric potential signal Δv, an electrode 260 of a reference interface E3w for measuring a reference electric potential for the bioelectric signal, the hydrogel 270, and an insulation layer 280.

The adhesive sheet 210 is a sheet formed of an insulating material that has both sides are coated with an adhesive material, and keeps the bioelectric signal measurement apparatus 100 in contact with the skin. That is, the bioelectric signal measurement apparatus 100 contacts the skin via the adhesive sheet 210, and the state of contact is maintained by the adhesive material of the adhesive sheet 210. To enable an electric connection between the bioelectric signal measurement apparatus 100 and the skin of the testee 110, holes are punched at positions of the adhesive sheet 210 where the bioelectric signal measurement apparatus 100 contacts the skin. That is, the bioelectric signal measurement apparatus 100 electrically interfaces with the skin of the testee 110 through the interfaces E1w (120), E1d (130), E2w (140), and E2d (150) to detect bioelectric signals. Accordingly, portions where the bioelectric signal measurement apparatus 100 electrically contacts the skin, that is, positions where the holes are formed in the adhesive sheet 210, are places where the electrodes 221, 222, 231, 232, 241, 242, 251, and 252 forming the interfaces E1w (120), E1d (130), E2w (140), and E2d (150) are located.

The electrodes 221, 222, 241, and 242 are electrodes forming the interfaces E1w (120) and E2w (140) for measuring the bioelectric signal, and therefore electrodes having a relatively low contact impedance are used as the electrodes 221, 222, 241, and 242 to reduce an influence of the motion artifact as described above. The electrodes 231, 232, 251, and 252 are electrodes forming the interfaces E1d (130) and E2d (150) for measuring the electric potential signal Δv, and therefore electrodes having a relatively high correlation between the contact impedance variation and the motion artifact are used for the electrodes 231, 232, 251, and 252 as described above. In FIG. 2, the electrodes 221, 222, 241, and 242 that measure the bioelectric signal are wet electrodes that electrically interface with the skin of the testee 110 via the hydrogel 270, whereas the electrodes 231, 232, 251, and 252 that measure the electric potential signal Δv are dry electrodes that directly contact the skin of the testee 110.

The bioelectric signal measurement apparatus 100 measures the bioelectric signal based on a difference between the electric potential values measured at the two interfaces E1w (120) and E2w (140) located at positions separated from each other by a predetermined distance. Accordingly, the electrodes 221 and 222 forming the interface E1w (120) and the electrodes 241 and 242 forming the interface E2w (140) are located at positions separated from each other by a predetermined distance to measure voltages of the bioelectric signal. The electrodes 231 and 232 of the interface E1d (130) for measuring the electric potential signal Δv are alternately arranged with the electrodes 221 and 222 of the interface E1w (120) for measuring the bioelectric signal at a spacing within the critical distance from the electrodes 221 and 222 of the interface E1w (120) so that the motion artifact measured using the electrodes 231 and 232 of the interface E1d (130) has almost the same shape as the motion artifact included in the bioelectric signal measured by the electrodes 221 and 222 of the interface E1w (120). Similarly, the electrodes 251 and 252 of the interface E2d (150) for measuring the electric potential signal Δv are alternately arranged with the electrodes 241 and 242 of the interface E2w (140) for measuring the bioelectric signal at a spacing within the critical distance from the electrodes 241 and 242 of the interface E2w (140) so that the motion artifact measured using the electrodes 251 and 252 of the interface E2d (150) has almost the same shape as the motion artifact included in the bioelectric signal measured by the electrodes 241 and 242 of the interface E2w (140).

When a single interface is formed by a plurality of electrodes as described above, not only almost the same shape of motion artifact on average may be obtained by alternately arranging the electrodes for measuring the bioelectric signal with the electrodes for measuring the electric potential signal Δv, but also the state in which the electrodes closely contact the skin during the measurement of the bioelectric signal may be maintained more easily compared to a single large electrode having the same area as the plurality of electrodes.

The reference interface E3w for measuring the reference electric potential for the bioelectric signal is formed of at least one electrode 260. The at least one electrode 260 of the reference interface E3w has the same structure as the electrodes 221, 222, 241, and 242 of the interfaces E1w (120) and E2w (140) for measuring the bioelectric signal. The reference interface E3w for measuring the reference electric potential for the bioelectric signal is located at a position separated a predetermined distance from the interfaces E1w (120) and E2w (140) for measuring the bioelectric signal so that the reference interface E3w is not influenced by the interfaces E1w (120) and E2w (140). In the contact surface 200 of FIG. 2, the position of the reference interface E3w is merely an example, and the reference interface E3w may be located at other positions.

The insulation layer 280 has a shape of a substrate and is formed of an insulating material that electrically isolates adjacent electrodes from each other to prevent current from flowing between the adjacent electrodes. In the contact surface 200 of the bioelectric signal measurement apparatus 100, the remaining area except for the areas where the electrodes and the hydrogel 270 are located is all formed by the insulation layer 280. In an example of the bioelectric signal measurement apparatus 100, the areas where the wet electrodes and the hydrogel 270 that closely contacts the wet electrodes are located may be configured to be concave to prevent an electrical connection between the hydrogel 270 and the dry electrodes. Since the dry electrodes and the wet electrodes are alternately arranged on the insulation layer 280, a cross-section of the insulation layer 280 has an uneven shape as illustrated in FIG. 2. The structure of the insulation layer 280 having an uneven shape as illustrated in FIG. 2 is merely an example, and the insulation layer 280 may have any one of numerous different structures. For example, the cross-section of the insulation layer 280 may have a flat shape like the insulation layer 1110 of the bioelectric signal measurement apparatus 100 illustrated in FIG. 11A.

As described above, the contact surface 200 where the bioelectric signal measurement apparatus 100 contacts the skin of the testee 110 includes the adhesive sheet 210, the electrodes of the interfaces E1w (120) and E2w (140) for measuring the bioelectric signal, the electrodes of the interfaces E1d (130) and E2d (150) for measuring the electric potential signal Δv, the electrode of the reference interface E3w (260), and the hydrogel 270. However, the shape of the contact surface 200, the types of the electrodes, and the arrangements of the electrodes of the bioelectric signal measurement apparatus 100 are not limited to those illustrated in FIG. 2, but may be modified in numerous ways as will be apparent to one of ordinary skill in the art.

Figure 4:
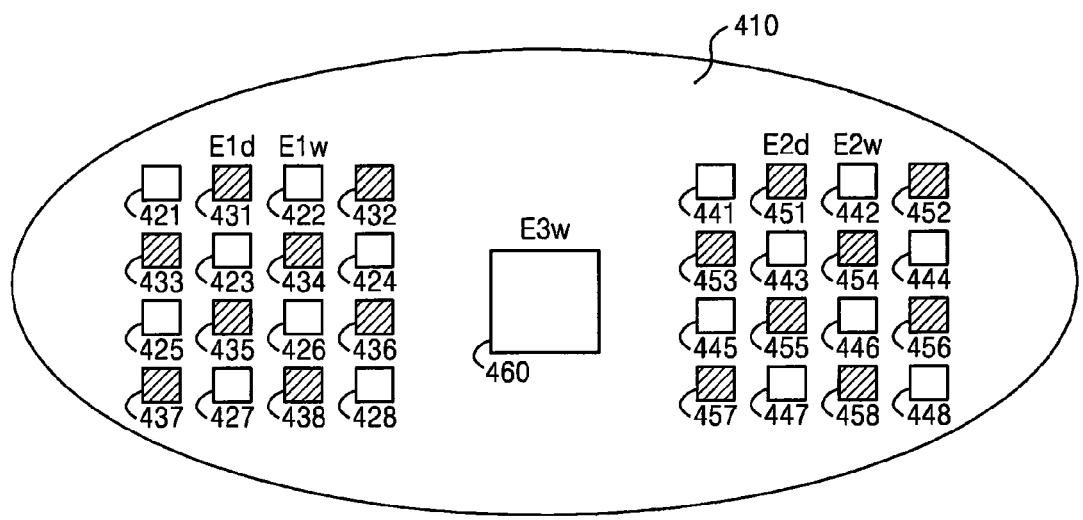
FIG. 4 schematically illustrates an example of a bottom surface of the bioelectric signal measurement apparatus of FIG. 1 on which electrodes forming interfaces of the bioelectric signal measurement apparatus of FIG. 1 are arranged.
Figure 5:
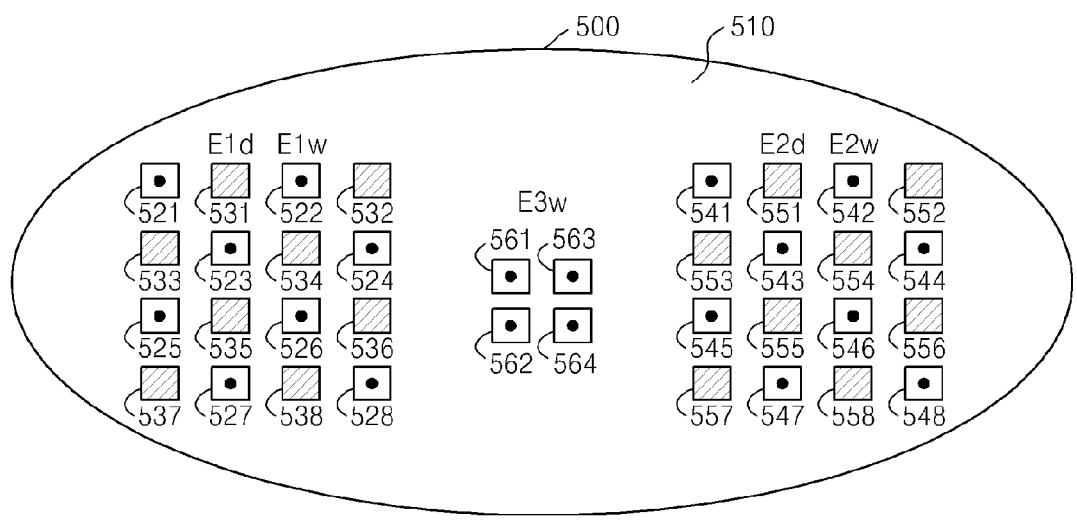
FIG. 5 schematically illustrates another example of a bottom surface of the bioelectric signal measurement apparatus of FIG. 1 on which electrodes forming interfaces of the bioelectric signal measurement apparatus of FIG. 1 are arranged.
Figure 7A:
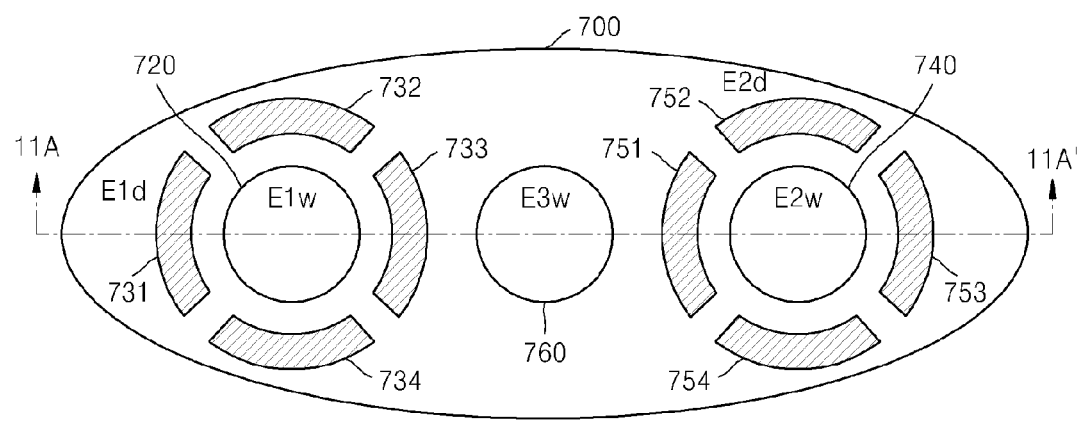
FIG. 7A schematically illustrates another example of a bottom surface of the bioelectric signal measurement apparatus of FIG. 1 on which electrodes forming interfaces of the bioelectric signal measurement apparatus of FIG. 1 are arranged.

FIGS. 4, 5, and 7A illustrate examples of bottom surfaces 400, 500, and 700 of the bioelectric signal measurement apparatus 100 on which the electrodes forming the interfaces of the bioelectric signal measurement apparatus 100 are arranged.

Referring to FIG. 4, the bottom surface 400 includes an adhesive sheet 410, electrodes 421-428 of an interface E1w for measuring a bioelectric signal, electrodes 441-448 of an interface E2w for measuring the bioelectric signal, electrodes 431-438 of an interface E1d for measuring an electric potential signal Δv, electrodes 451-458 of an interface E2d for measuring the electric potential signal Δv, and an electrode 460 of a reference interface E3w for measuring a reference electric potential for the bioelectric signal.

As described with respect to FIG. 2, the two interfaces E1w and E2w for measuring the bioelectric signal measure electric potential values of the bioelectric signal at positions separated from each other by a predetermined distance. The electrodes 431-438 of the interface E1d for measuring the electric potential signal Δv are alternately arranged with the electrodes 421-428 of the interface E1w for measuring the bioelectric signal at a spacing within the critical distance from the electrodes 421-428 of the interface E1w. The electrodes 421-428 of the interface E1w are at the same electric potential and form a single interface, and the electrodes 431-438 of the interface E1d are at the same electric potential and form a same interface. Since the electrodes 421-428 of the interface E1w and the electrodes 431-438 of the interface E1d are alternately with each other at a spacing within the critical distance from each other, the motion artifact measured using the electrodes 431-438 of the interface E1d has almost the same shape as the motion artifact included in the bioelectric signal measured by the electrodes 421-428 of the interface E1w. Similarly, the electrodes 451-458 of the interface E2d for measuring the electric potential signal Δv are alternately arranged with the electrodes 441-448 of the interface E2w for measuring the bioelectric signal at a spacing within the critical distance from the electrodes 441-448 of the interface E2w, so the motion artifact measured using the electrodes 451-458 of the interface E2d has almost the same shape as the motion artifact included in the bioelectric signal measured by the electrodes 441-448 of the interface E2w.

The electrode 460 of the reference interface E3w for measuring a reference electric potential for the bioelectric signal is separated by a predetermined distance from the interfaces E1w and E2w for measuring the bioelectric signal so that the interface E3w is not affected by the interfaces E1w and E2w. The electrodes 421-428 and 441-448 of the interfaces E1w and E2w for measuring the bioelectric signal and the electrode 460 of the reference interface E3w for measuring the reference electric potential for the bioelectric signal are wet electrodes that contact the skin via the hydrogel 270, whereas the electrodes 431-438 and 451-458 of the interfaces E1d and E2d for measuring the electric potential signal Δv are dry electrodes that directly contact the skin.

Holes are punched in the adhesive sheet 410 where each electrode is located, and the remaining area the adhesive sheet 410 is formed of an insulating material. As illustrated in FIG. 2, the wet electrodes and the dry electrodes are electrically isolated from each other by the insulating material of the insulation layer.

Referring to FIG. 5, the bottom surface 500 includes an adhesive sheet 510, electrodes 521-528 of an interface E1w for measuring a bioelectric signal, electrodes 541-548 of an interface E2w for measuring the bioelectric signal, electrodes 531-538 of an interface E1d for measuring an electric potential signal Δv, electrodes 551-558 of an interface E2d for measuring the electric potential signal Δv, and electrodes 561-564 of a reference interface E3w.

The interfaces E1w and E2w for measuring the bioelectric signal, the interfaces E1d and E2d for measuring the electric potential signal Δv, and the reference interface E3W for measuring the reference electric potential for the bioelectric signal are arranged like the interfaces E1w, E2w, E1d, E2d, and E3w of FIG. 4. However, unlike FIG. 4, the reference interface E3w for measuring the reference electric potential for the bioelectric signal of FIG. 5 is formed of a plurality of electrodes 561-564 having the same electric potential, rather than being formed of single electrode 560 like the reference interface E3w of FIG. 4.

Unlike the electrodes of FIG. 4, the electrodes 521-528 and 541-548 of the interfaces E1w and E2w for measuring the bioelectric signal of FIG. 5 and the electrodes 561-564 of the reference interface E3w for measuring the reference electric potential for the bioelectric signal are not wet electrodes electrically interfacing with the skin via the hydrogel 270, but are electrodes formed of a conductive material like the electrodes 531-538 and 551-558 of the interfaces E1d and E2d for measuring the electric potential signal $\Delta v$. The electrodes 521-528, 541-548, and 561-564 of the interfaces E1w, E2w, and E3w each have a sharp protrusion to reduce the influence of the motion artifact on the bioelectric signal without the need to use the hydrogel 270 that maintains a low contact impedance with the skin. The sharp protrusions are indicated by black dots in the center of the electrodes 521-528, 541-548, and 561-564 of the interfaces E1w, E2w, and E3w in FIG. 5. The sharp protrusions of the electrodes 521-528, 541-548, and 561-564 of the interfaces E1w, E2w, and E3w penetrate the stratum corneum of the skin and make electrical contact with the epidermis beneath the stratum corneum to provide a contact impedance lower than the contact impedance of the electrodes 531-538 and 551-558 of the interfaces E1d and E2d that are also formed of a conductive material but contact only the surface of the skin.

Figure 6:
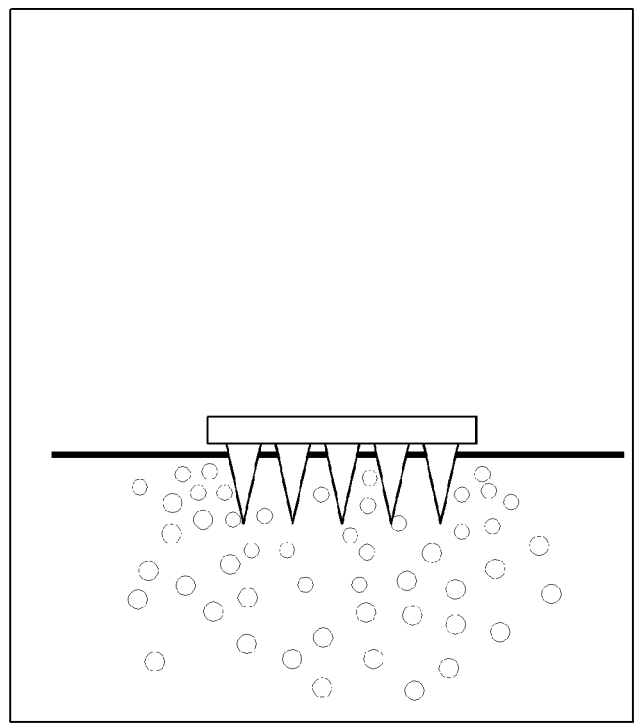
FIG. 6 is a cross-sectional view illustrating an example of a shape of sharp protrusions of electrodes forming interfaces E1w, E2w, and E3w of FIG. 5, and an example of a state in which an electrodes having sharp protrusions penetrate the stratum corneum of the skin and make electrical contact with the epidermis beneath the stratum corneum.

FIG. 6 is a cross-sectional view illustrating an example of the shape of the sharp protrusions of the electrodes forming the interfaces E1w, E2w, and E3w of FIG. 5, and an example of a state in which electrodes having sharp protrusions penetrate the stratum corneum of the skin and make electrical contact with the epidermis beneath the stratum corneum.

The bottom surface 700 of FIG. 7A includes an electrode 720 of an interface E1w for measuring a bioelectric signal, an electrode 740 of an interface E2w for measuring the bioelectric signal, electrodes 731-734 of an interface E1d for measuring an electric potential signal $\Delta v$, electrodes 751-754 of an interface E2d for measuring the electric potential signal $\Delta v$, and an electrode 760 of a reference interface E3w for measuring a reference electric potential for the bioelectric signal.

Unlike FIGS. 4 and 5, each of the interfaces E1w and E2w for measuring the bioelectric signal of FIG. 7A is formed of a single electrode. The electrode 720 of the interface E1w and the electrode 740 of the interface E2w measure electric potential values of the bioelectric signal at positions separated from each other by a predetermined distance, and are respectively surrounded by the electrodes 731-734 of the interface E1d for measuring the electric potential signal $\Delta v$ and the electrodes 751-754 of the interface E2d for measuring the electric potential signal $\Delta v$. The electrodes 731-734 of the interface E1d for measuring the electric potential signal $\Delta v$ that surround the electrode 720 of the interface E1w for measuring the bioelectric signal are respectively arranged at a spacing within the critical distance from the electrode 720 of the interface E1w for measuring the bioelectric signal, so the motion artifacts input to the interfaces E1w and E1d have almost the same shape on average. The electrodes 751-754 of the interface E2d for measuring the electric potential signal $\Delta v$ that surround the electrode 740 of the interface E2w for measuring the bioelectric signal are respectively arranged at a spacing within the critical distance from the electrode 740 of the interface E2w for measuring the bioelectric signal, so the motion artifacts input to the interfaces E2w and E2d have almost the same shape on average. The electrode 760 of the reference interface E3w for measuring the reference electric potential of FIG. 7A is separated by a predetermined distance from the electrode 720 of the interface E1w and the electrode 740 of the interface E2w for measuring the bioelectric signal so that the reference interface E3w is not influenced by the interfaces E1w and E2w.

The electrodes 720 and 740 of the interfaces E1w and E2w for measuring the bioelectric signal and the electrode 760 of the reference interface E3w for measuring a reference electric potential for the bioelectric signal may be formed of wet electrodes that contact the skin via the hydrogel 270 as illustrated in FIG. 4, or electrodes having sharp protrusions that penetrate the stratum corneum of the skin and make electrical contact with the epidermis beneath the stratum corneum without the hydrogel 270 as illustrated in FIG. 5. The electrodes 731-734 and 751-754 of the interfaces E1d and E2d for measuring the electric potential signal $\Delta v$ are dry electrodes that directly contact the skin.

Figure 7B:
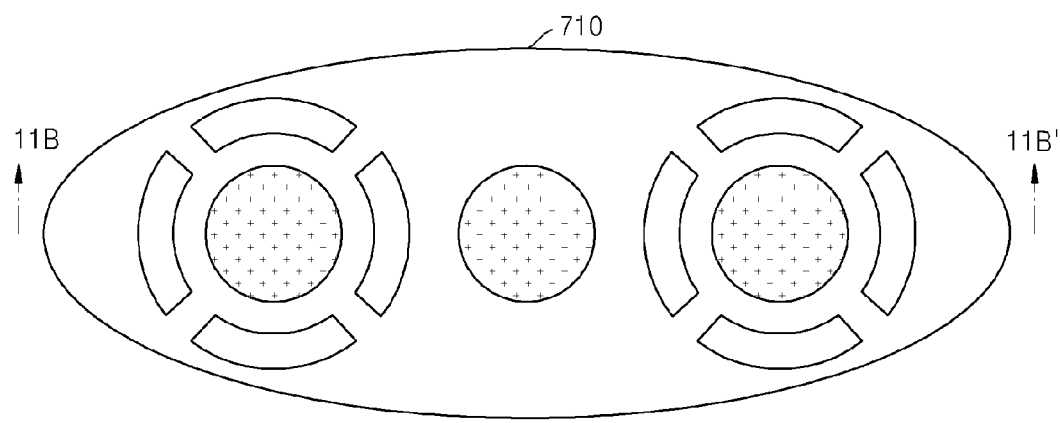
FIG. 7B illustrates an example of an adhesive sheet attached to the bottom surface of the bioelectric signal measurement apparatus of FIG. 7A.

FIG. 7B illustrates an example of an adhesive sheet 710 attached to the bottom surface of the bioelectric signal measurement apparatus 100 of FIG. 7A that enables the interfaces of the bioelectric signal measurement apparatus 100 to be attached to the skin of the testee 110 and keeps the interfaces attached to the skin. The adhesive sheet 710 has holes where the electrodes of FIG. 7A are located so the electrodes of the bioelectric signal measurement apparatus 100 contact the skin through the holes of the adhesive sheet 710.

Referring back to FIG. 1, the motion artifact extraction unit 160 receives the electric potential signal $\Delta v$ from the interfaces E1d (130) and E2d (150) and extracts a signal proportional to a motion artifact. As described above, the electric potential signal $\Delta v$ is measured by applying a predetermined current i0 to the skin and obtaining a change $\Delta v$ in the electric potential produced thereby. The detailed operation of the motion artifact extraction unit 160 that extracts a signal proportional to a motion artifact using the electric potential signal $\Delta v$ detected by the interfaces E1d (130) and E2d (150) will be described below with reference to FIG. 8.

Figure 8:
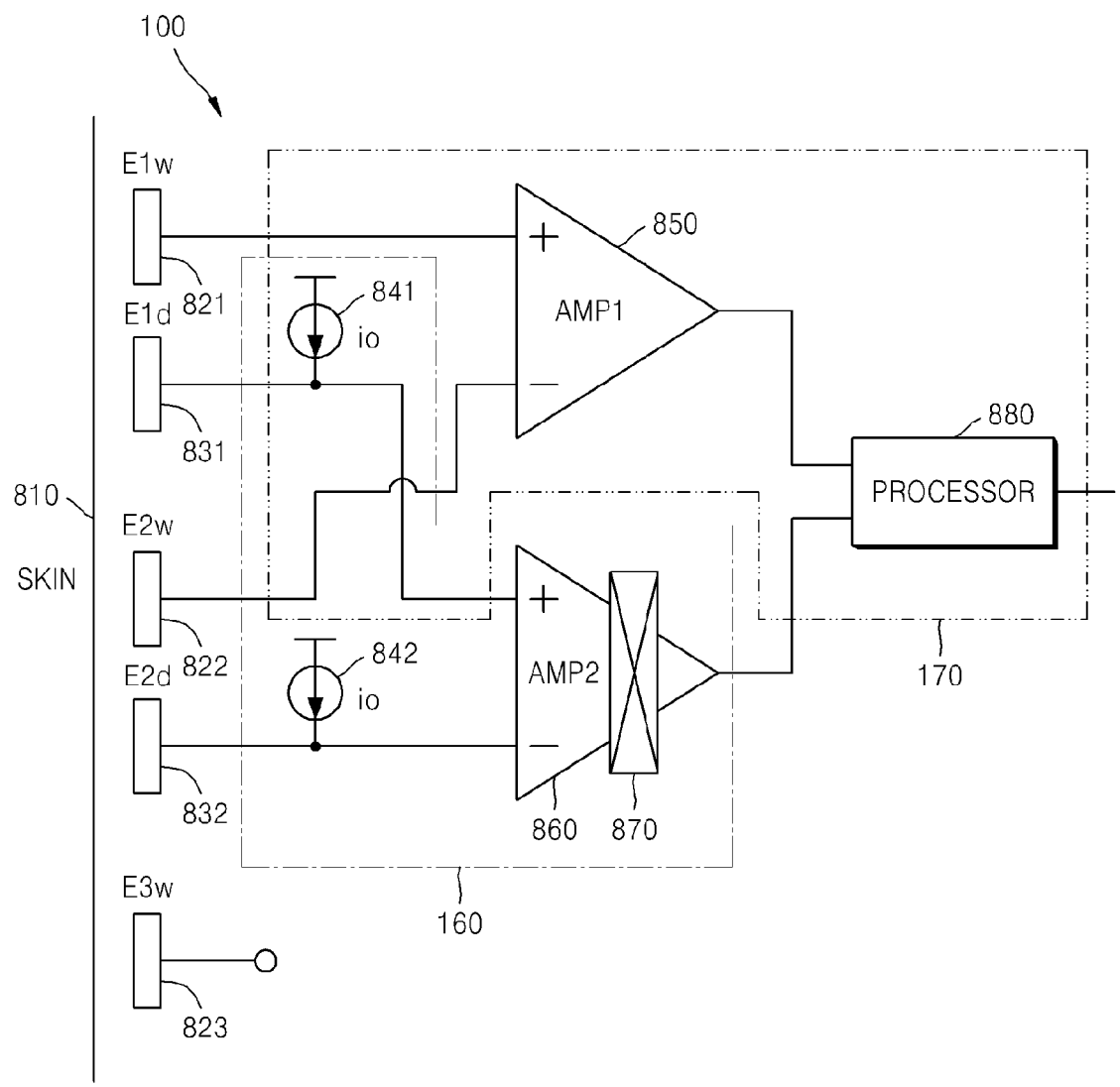
FIG. 8 illustrates an example of a circuit of the bioelectric signal measurement apparatus of FIG. 1.

FIG. 8 illustrates an example of a circuit of the bioelectric signal measurement apparatus 100 of FIG. 1. The bioelectric signal measurement apparatus 100 of FIG. 8 contacts a skin 810 of the testee 110 via interfaces E1w (821), E2w (822), E3w (823), E1d (831), and E2d (832). The bioelectric signal measurement apparatus 100 of FIG. 8 includes the interfaces E1w (821) and E2w (822) for measuring the bioelectric signal, the interface E3w for measuring a reference electric potential for the bioelectric signal, the interfaces E1d (831) and E2d (832) for measuring the electric potential signal $\Delta v$, bias current sources 841 and 842, differential amplifiers 850 and 860, a demodulator 870, and a processor 880.

Referring to FIG. 8, the motion artifact extraction unit 160 includes the bias current sources 841 and 842, the differential amplifier 860, and the demodulator 870. The motion artifact extraction unit 160 applies a predetermined current i0 modulated at a frequency fc that does not overlap with the frequency range of a bioelectric signal to the interfaces E1d (831) and E2d (832) for measuring the electric potential signal $\Delta v$ using the bias current sources 841 and 842. Accordingly, the electric potential signal $\Delta v$ detected by the interfaces E1d (831) and E2d (832) is influenced by the applied current i0 and is thus modulated at the frequency fc. The electric potential signal Δv detected by the interfaces E1d (831) and E2d (832) has a very small amplitude so that the signal needs to be amplified. Thus, the motion artifact extraction unit 160 differentially amplifies the electric potential values obtained from the interfaces E1d (831) and E2d (832) using the differential amplifier 860 and demodulates an amplified signal to recover the original signal by using the demodulator 870, thereby extracting a signal proportional to a motion artifact. The motion artifact extraction unit 160 outputs the signal proportional to a motion artifact extracted through the above process to the bioelectric signal extraction unit 170.

The bioelectric signal extraction unit 170 of FIG. 1 extracts a bioelectric signal including a motion artifact using the signals obtained from the interfaces E1w (120) and E2w (140) and removes the motion artifact from the bioelectric signal including a motion artifact, thereby detecting an actual bioelectric signal of the testee 110. Since the signal extracted by the motion artifact extraction unit 160 is proportional to the motion artifact included in the bioelectric signal obtained from the interfaces E1w (120) and E2w (140), the bioelectric signal extraction unit 170 is able to remove the motion artifact from the bioelectric signal including the motion artifact by using the signal extracted by the motion artifact extraction unit 160. A detailed operation of the bioelectric signal extraction unit 170 that removes the motion artifact included in the bioelectric signal obtained from the interfaces E1w (120) and E2w (140) will be described below with reference to FIG. 8.

Referring to FIG. 8, the bioelectric signal extraction unit 170 includes the differential amplifier 850 and the processor 880. The differential amplifier 850 of the bioelectric signal extraction unit 170 receives the signals (electric potential values) measured through the interfaces E1w (821) and E2w (822) for measuring the bioelectric signal and differentially amplifies the received signals, thereby outputting a bioelectric signal including a motion artifact. To avoid distortion of the signals measured through the interfaces E1w (821) and E2w (822) due to the influence of low frequency noise during an amplification process of the signals, the bioelectric signal extraction unit 170 may use a method of modulating the measured signals into a high frequency signal before amplifying the signals, amplifying the modulated signals, and demodulating amplified signals into the original signals by using a demodulator. The modulation frequency of the measured signals is different from the frequency fc of the bias current sources 841-842 of the motion artifact extraction unit 160 so that the frequency range of the measured signals does not overlap with the frequency range of the electric potential signal Δv.

The processor 880 of the bioelectric signal extraction unit 170 controls a process of receiving the bioelectric signal including the motion artifact output from the differential amplifier 850 and the signal proportional to the motion artifact output from the motion artifact extraction unit 160, and removing the motion artifact from the bioelectric signal including the motion artifact using the signal proportional to the motion artifact. The processor 880 performs an operation needed for removing the motion artifact from the bioelectric signal including the motion artifact.

The processor 880 of the bioelectric signal extraction unit 170 includes an adaptive filter to effectively remove the motion artifact. The adaptive filter is a digital filter having adjustable filter coefficients that are adjusted according to a value fed back to the adaptive filter. The adaptive filter removes noise by estimating noise that actually changes by adjusting the filter coefficients considering the characteristics of an input signal, an environment, and a result signal to random noise having no predetermined pattern. In this example, the adaptive filter adjusts the filter coefficients based on a bioelectric signal free of the motion artifact that is fed back to the adaptive filter, and filters the signal proportional to the motion artifact using the adjusted filter coefficients, thereby estimating a motion artifact and outputting an estimated motion artifact signal close to an actual motion artifact. The processor 880 further includes an operator that receives the estimated motion artifact signal output from the adaptive filter and removes the estimated motion artifact signal from the amplified bioelectric signal including the motion artifact, thereby obtaining an actual bioelectric signal free of the motion artifact.

Figure 9:
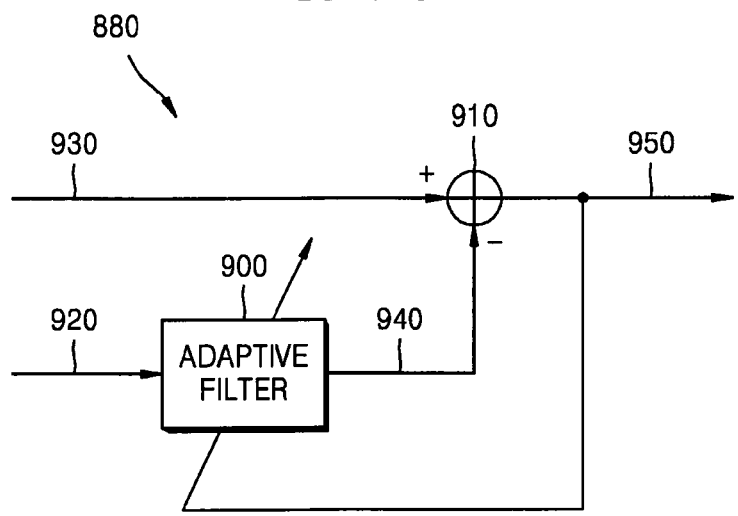
FIG. 9 illustrates an example of a circuit of the processor of the bioelectric signal measurement apparatus of FIG. 1.

FIG. 9 illustrates an example of a circuit of the processor 880 of the bioelectric signal measurement apparatus 100 of FIG. 1. The processor 880 of FIG. 9 includes an adaptive filter 900 and an operator 910.

The processor 880 of the bioelectric signal measurement apparatus 100 receives a signal 920 proportional to the motion artifact output from the motion artifact extraction unit 160 and a bioelectric signal 930 including the motion artifact output from the amplifier 850. The adaptive filter 900 receives the signal 920 proportional to the motion artifact and a bioelectric signal 950 free of the motion artifact that is fed back to the adaptive filter 900 and adjusts the filter coefficients of the adaptive filter 900 based on the bioelectric signal 950 free of the motion artifact. The adaptive filter 900 filters the signal 920 proportional to the motion artifact by using the adjusted filter coefficients to estimate the motion artifact, and outputs an estimated motion artifact signal 940 close to an actual motion artifact. The operator 910 receives the bioelectric signal 930 including the motion artifact output from the amplifier 850 and the estimated motion artifact signal 940 close to an actual motion artifact output from the adaptive filter 900, and performs an operation of removing the estimated motion artifact signal 940 from the bioelectric signal 930 including the motion artifact. As a result of the operation, the operator 910 outputs the signal 950 free of the motion artifact that is fed back to the adaptive filter 900. Thus, the processor 880 of the bioelectric signal extraction unit 170 obtains an actual bioelectric signal free of the motion artifact through the above-described process.

The bioelectric signal measured as described above may be used for monitoring the state of a human body or diagnosing or treating a variety of types of diseases. For example, the bioelectric signal measurement apparatus 100 may measure an electrocardiogram (ECG), which is one example of a bioelectric signal, through the interfaces E1w (120), E1d (130), E2w (140), and E2d (150) attached to the body of the testee 110. When the heart of the testee 110 repeatedly contracts and relaxes as the heart beats, a very small change in electric potential is generated on the skin of the testee 110. This electric activity presented in a graph form is called an ECG. An expert who reviews ECG data measured by the bioelectric signal measurement apparatus 100 may diagnose and treat a cardiac disease such as myocardial infarction or arrhythmia, or may monitor electrical activity of the heart of the testee 110 to prevent illness due to cardiac disease. To diagnose and treat a disease based on a bioelectric signal, a high reliability of a measured bioelectric signal is required. Thus, it is important to remove a motion artifact from the measured bioelectric signal by measuring a motion artifact that is as similar as possible to the actual motion artifact and to obtain an accurate bioelectric signal.

In an apparatus for measuring a bioelectric signal in related art, the same electrodes, or electrodes having the same structure, are used to measure the bioelectric signal and the electric potential signal Δv without taking into account the correlation between the contact impedance variation and the motion artifact and an electrode type so that accurate measurement of the bioelectric signal is not possible.

Figure 10:
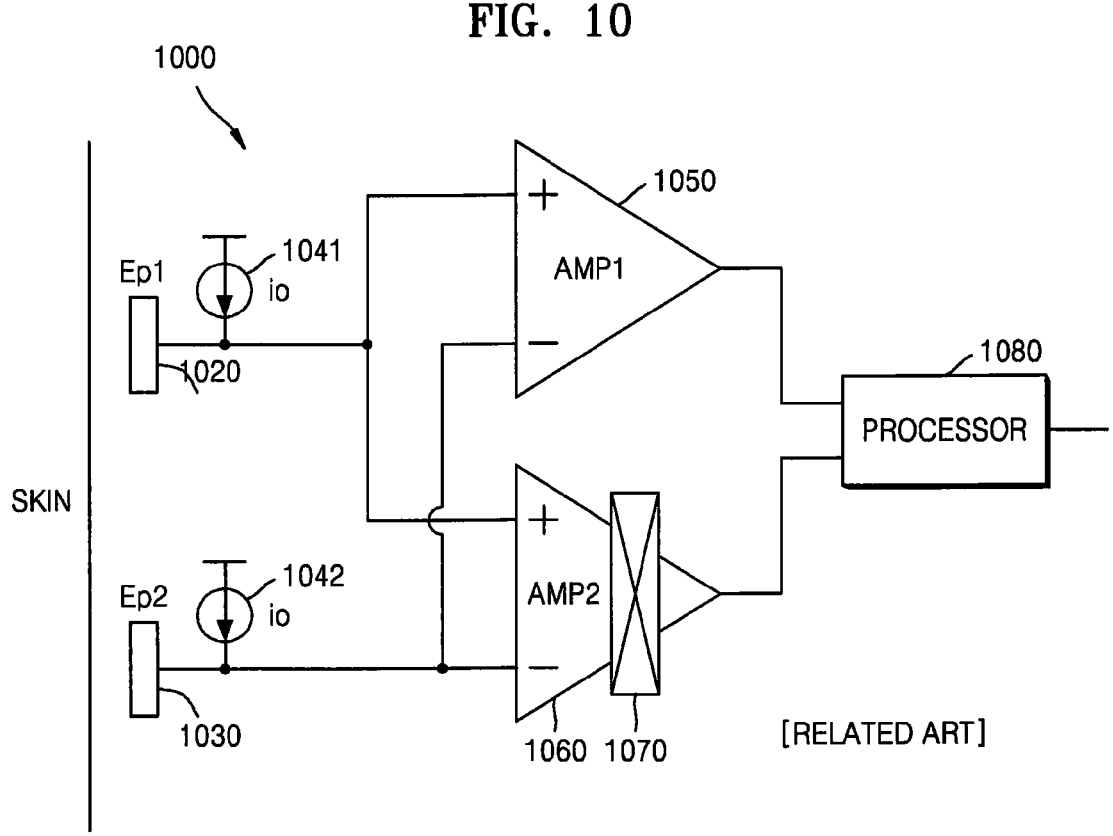
FIG. 10 illustrates an example a circuit of a bioelectric signal measurement apparatus according to related art.

FIG. 10 illustrates an example of a circuit of a bioelectric signal measurement apparatus 1000 in related art. The bioelectric signal measurement apparatus 1000 includes bias current sources 1041 and 1042, differential amplifiers 1050 and 1060, a demodulator 1070, and a processor 1080 that are basically the same as the bias current sources 841 and 842, the differential amplifiers 850 and 860, the demodulator 870, and the processor 880 of the bioelectric signal measurement apparatus 100 of FIG. 8, and thus will not be described in detail here. However, unlike the bioelectric signal measurement apparatus 100 of FIG. 8, the bioelectric signal measurement apparatus 1000 of FIG. 10 measures the bioelectric signal and the electric potential signal Δv using the same electrodes Ep1 (1020) and Ep2 (1030). The bioelectric signal measurement apparatus 1000 typically uses wet electrodes contacting the skin via a hydrogel like the hydrogel 270 as the electrodes Ep1 (1020) and Ep2 (1030) for measuring the bioelectric signal and the electric potential signal Δv. When the bioelectric signal is measured using the hydrogel between the electrodes Ep1 (1020) and Ep2 (1030) and the skin, the influence of the motion artifact on the bioelectric signal is reduced due to a low contact impedance between the electrodes Ep1 (1020) and Ep2 (1030) and the skin so that a relatively uniform and stable bioelectric signal may be obtained compared to a case of using dry electrodes as the electrodes Ep1 (1020) and Ep2 (1030).

However, when the electric potential signal Δv is measured using the same electrodes that are used to measure the bioelectric signal, or using the same type of electrodes that are used to measure the bioelectric signals, that is, wet electrodes contacting the skin via the hydrogel, since the influence of the motion artifact is difficult to accurately measure due to a low contact impedance between the wet electrodes and the skin, the motion artifact will not be properly removed from the measured bioelectric signal. For example, when an ECG waveform is monitored using a bioelectric signal measurement apparatus, if the bioelectric signal is distorted due to the motion artifact, it is difficult to accurately determine the state of the heart so that the life of a patient may be endangered. Thus, it is important to accurately measure the bioelectric signal by taking into account as closely as possible the influence of the actual motion artifact. When the bioelectric signal is measured using the bioelectric signal measurement apparatus 100 of FIG. 8, the bioelectric signal may be accurately measured by using the interfaces that take into account the correlation between the contact impedance variation and the motion artifact and an electrode type.

Figure 11A:
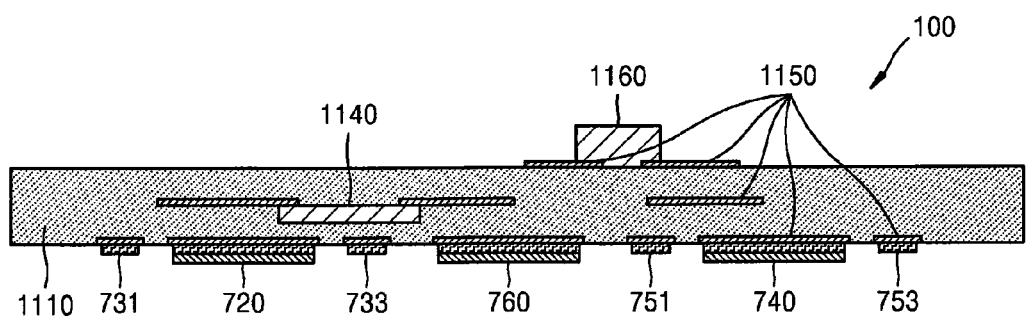
FIG. 11A is a cross-sectional view of the bioelectric signal measurement apparatus of FIG. 7A taken along the line 11A-11A' in FIG. 7A.

FIG. 11A is a cross-sectional view of the bioelectric signal measurement apparatus 100 of FIG. 7A taken along the line 11A-11A' in FIG. 7A. Referring to FIG. 11A, the bioelectric signal measurement apparatus 100 includes an insulation layer 1110, electrodes 731, 733, 751, and 753 for measuring the electric potential signal Δv of the motion artifact, electrodes 720 and 740 for measuring the bioelectric signal, an electrode 760 for measuring a reference electric potential for the bioelectric signal, an integrated circuit 1140, which, for example, may be a thinned application-specific integrated circuit (ASIC), conductive wires 1150, and various passive devices 1160, such as resistors, or capacitors, or inductors, or any other passive devices known to one of ordinary skill in the art, or any combination thereof.

The insulation layer 1110, like the insulation layer 280 of FIG. 2, electrically isolates the electrodes 720 and 740 for measuring the bioelectric signal and the electrode 760 for measuring the reference electric potential for the bioelectric signal from the electrodes 731, 733, 751, and 753 for measuring the electric potential signal Δv of the motion artifact. Also, the insulation layer 1110 prevents electrical coupling or interference between the integrated circuit 1140 and the conductive wires 1150 of the bioelectric signal measurement apparatus 100.

The electrodes 731 and 733 for measuring the electric potential signal Δv of the motion artifact are electrodes having the same electric potential forming the interface E1d, and are arranged at a spacing within the critical distance from the electrode 720 for measuring the bioelectric signal so the motion artifact measured by the electrodes 731 and 733 has almost the same shape on average as the motion artifact measured by the electrode 720. Similarly, the electrodes 751 and 753 for measuring the electric potential signal Δv of the motion artifact are electrodes having the same electric potential for forming the interface E2d, and are arranged at a spacing within the critical distance from the electrode 740 for measuring the bioelectric signal so the motion artifact measured by the electrodes electrodes 751 and 753 has almost the same shape on average as the motion artifact measured by the electrode 740. The electrodes 731, 733, 751, and 753 for measuring the electric potential signal Δv of the motion artifact are dry electrodes that directly contact the skin of the testee 110 without the hydrogel 270. The dry electrodes may be flat plates formed of a highly conductive metal, such as gold (Au), silver (Ag), platinum (Pt), or any other highly conductive metal know to one of ordinary skill in the art. However, any other type of dry electrode known to one of ordinary skill in the art may be used as the dry electrodes.

The electrodes 720 and 740 for measuring the bioelectric signal are electrodes respectively forming the interfaces E1w and E2w, and are separated from each other by a predetermined distance. The electrode 760 for measuring the reference electric potential for the bioelectric signal is an electrode forming the reference interface E3w, and is separated from the electrodes 720 and 740 respectively forming the interfaces E1w and E2w by a predetermined distance so the reference interface E3w is not influenced by the interfaces E1w and E2w. The electric potential values measured by the electrodes 720 and 740 are differentially amplified to obtain the bioelectric signal. The electrodes 720, 740, and 760 are wet electrodes that contact the skin via the hydrogel 270, and may be a flat plate formed of metal coated with a material having a superior conductivity, such as a flat plate formed of silver (Ag) coated with silver chloride (AgCl), or any other type of wet electrode known to one of ordinary skill in the art. Alternatively, the electrodes 720, 740, and 760 may be electrodes having sharp protrusions that penetrate the stratum corneum of the skin and make electrical contact points with the epidermis beneath the stratum corneum without the hydrogel 270.

The integrated circuit 1140 is a semiconductor chip implemented by digital circuits, analog circuits, or both. The bias current sources 841 and 842, the differential amplifiers 850 and 860, the modulator 870, and the processor 880 illustrated in FIG. 8 may be located in the integrated circuit 1140. The motion artifact extraction unit 160 and the bioelectric signal extraction unit 170 of the bioelectric signal measurement apparatus 100 are implemented by the integrated circuit 1140, the conductive wires 1150, and the various passive devices 1160.

Figure 11B:
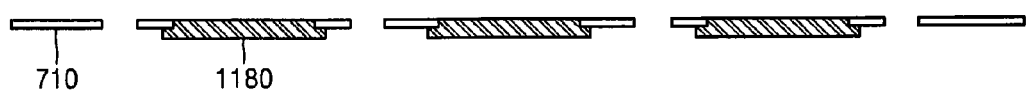
FIG. 11B is a cross-sectional view of the adhesive sheet of FIG. 7B taken along the line 11B-11B' in FIG. 7B.

FIG. 11B is a cross-sectional view of the adhesive sheet 710 of FIG. 7B taken along the line 11B-11B' in FIG. 7B. In FIG. 11B, an adhesive sheet 710 and a hydrogel 1180 are illustrated. Referring to FIG. 11B, the adhesive sheet 710 is a sheet formed of an insulating material having both surfaces coated with an adhesive material, like the adhesive sheet 210 of FIG. 2, and is used to attach the bioelectric signal measurement apparatus 100 to the skin and keep the bioelectric signal measurement apparatus 100 in contact with the skin. Holes are formed in the adhesive sheet 710 where the electrodes 731, 733, 751, and 753 of FIG. 11A for measuring the electric potential signal Δv are located, so the electrodes 731, 733, 751, and 753 of FIG. 11A for measuring the electric potential signal Δv directly contact the skin. When the electrodes 720 and 740 of FIG. 11A for measuring the bioelectric signal and the electrode 760 of FIG. 11A for measuring the reference electric potential for the bioelectric signal are wet electrodes, the electrodes 720, 740, and 760 of FIG. 11A for measuring the bioelectric signal contact the skin via the hydrogel 1180 so that the areas where the electrodes 720, 740, and 760 of FIG. 11A for measuring the bioelectric signal are located are filled with the hydrogel 1180.

Figure 12:
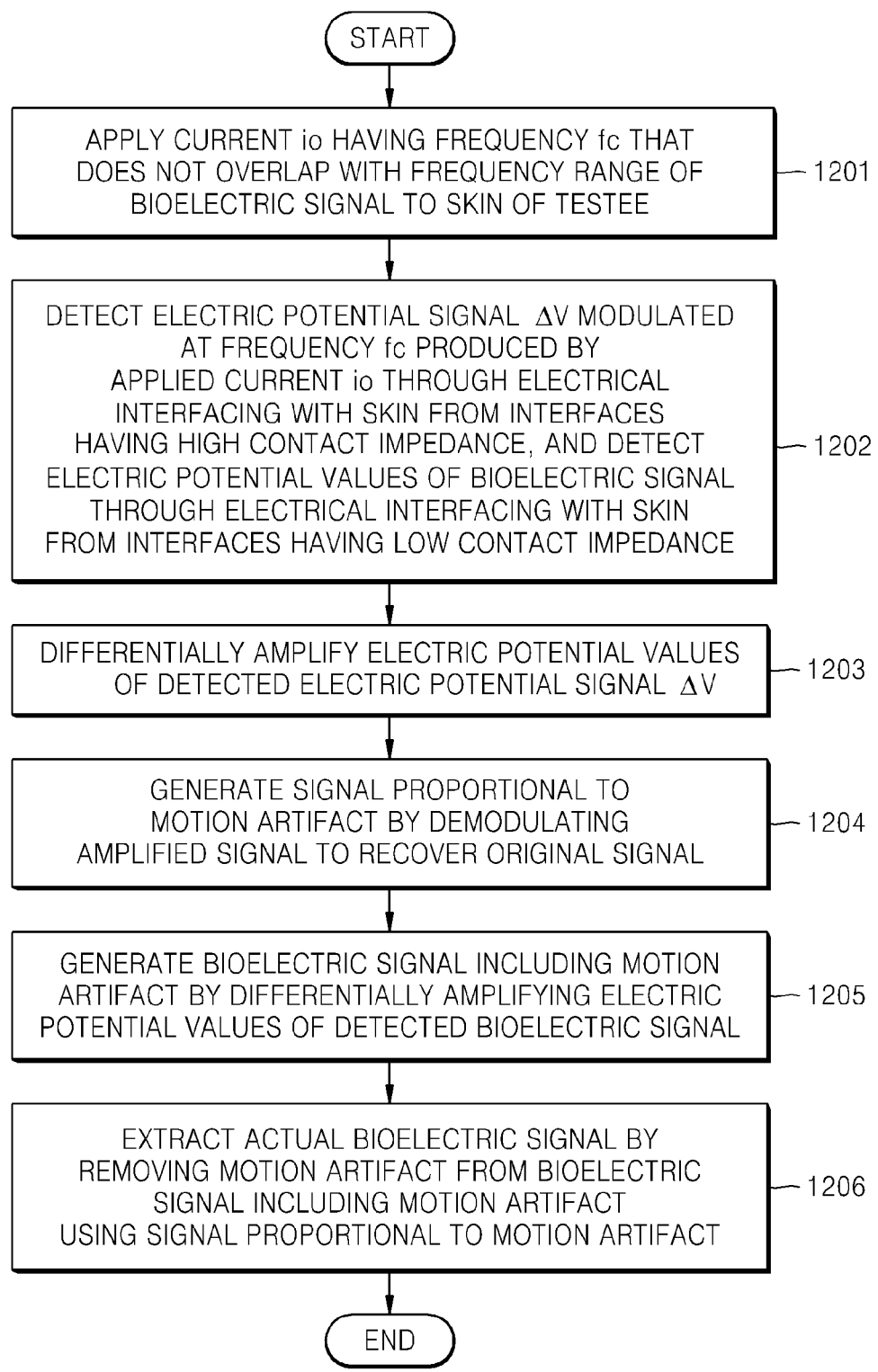
FIG. 12 is a flowchart of an example of a method of measuring bioelectric signals.

FIG. 12 is a flowchart for explaining an example of a method of measuring bioelectric signals. The method of measuring bioelectric signals of FIG. 12 includes operations to be performed using the bioelectric signal measurement apparatus 100 of FIG. 1. Thus, although omitted below, the above description of the bioelectric signal measurement apparatus 100 of FIG. 1 is also applicable to the method of measuring bioelectric signals of FIG. 12.

In operation 1201, the bioelectric signal measurement apparatus 100 applies the current i0 having the frequency fc that does not overlap with the frequency range of the bioelectric signal through the interfaces E1d (130) and E2d (150) that contact the skin of the testee 110. In operation 1202, the bioelectric signal measurement apparatus 100 detects the electric potential signal Δv modulated at the frequency fc produced by the current i0 applied in operation 1201 through the electrical interfacing with the skin of the testee 110 from the interfaces E1d (130) and E2d (150) having a high contact impedance, and detects the electric potential values of the bioelectric signal through the electrical interfacing with the skin of the testee 110 from the interfaces E1w (120) and E2w (140) having a low contact impedance, that is, a contact impedance that is lower than the contact impedance of the interfaces E1d (130) and E2d (150) as discussed in detail above. In operation 1203, the motion artifact extraction unit 160 of the bioelectric signal measurement apparatus 100 differentially amplifies the electric potential signal Δv detected in operation 1202. In operation 1204, the motion artifact extraction unit 160 demodulates the signal amplified in operation 1203 to recover the original signal to generate a signal proportional to the motion artifact. In operation 1205, the bioelectric signal extraction unit 170 differentially amplifies the electric potential values of the bioelectric signal detected in operation 1202 to generate the bioelectric signal including the motion artifact. In operation 1206, the bioelectric signal extraction unit 170 extracts an actual bioelectric signal by removing the motion artifact from the bioelectric signal including the motion artifact generated in operation 1205 using the signal proportional to the motion artifact generated in operation 1204. Although a particular sequence of operations is illustrated in FIG. 12, other sequences are also possible as will be apparent to one of ordinary skill in the art. For example, operation 1205 may be performed before operation 1203, or operations 1203 and 1204 may be performed in parallel with operation 1205.

As described above, a bioelectric signal of a testee may be accurately measured by extracting a motion artifact included in the bioelectric signal generated by movement of the testee during the measurement of the bioelectric signal, and removing the extracted motion artifact from the bioelectric signal.

The motion artifact extraction unit 160, the bioelectric signal extraction unit 170, the signal processor 180, the processor 880, the adaptive filter 900, the operator 910, and the processor 1080 described above may be implemented using one or more hardware components, one or more software components, or a combination of one or more hardware components and one or more software components.

A hardware component may be, for example, a physical device that physically performs one or more operations, but is not limited thereto. Examples of hardware components include bias current sources, differential amplifiers, demodulators, adaptive filters, operators, integrated circuits, passive devices, low-pass filters, high-pass filters, band-pass filters, analog-to-digital converters, digital-to-analog converters, data storage devices, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described therein are to be considered in a descriptive sense only, and not for purposes of limitation. Descriptions of features and aspects in each example are to be considered as being applicable to similar features and aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A bioelectric signal measurement apparatus, comprising:
    a first interface including at least one electrode configured to detect a bioelectric signal of a testee through electrical interfacing with a skin of the testee;
    a second interface including at least one electrode configured to detect only a motion artifact signal different from the bioelectric signal through electrical interfacing with the skin, the at least one electrode included in the second interface electrically interfacing with the skin in a state that is different from a state in which the at least one electrode included in the first interface electrically interfaces with the skin; and
    a signal processor configured to remove, from the detected bioelectric signal, a motion artifact between the first interface and the skin using the detected motion artifact signal
    wherein an impedance of the at least one electrode included in the second interface due to the electrical interfacing with the skin is larger than an impedance of the at least one electrode included in the first interface due to the electrical interfacing with the skin.

2. The bioelectric signal measurement apparatus of claim 1, wherein the at least one electrode included in the first interface is further configured to electrically interface with the skin through a predetermined material, and the at least one electrode included in the second interface is further configured to electrically interface directly with the skin, causing the impedance of the at least one electrode included in the second interface to be larger than the impedance of the at least one electrode included in the first interface.

3. The bioelectric signal measurement apparatus of claim 1, wherein the at least one electrode included in the first interface comprises a sharp protrusion configured to penetrate a stratum corneum of the skin, and the at least one electrode included in the second interface comprises a flat plate configured to contact a surface of the skin.

4. The bioelectric signal measurement apparatus of claim 1, wherein the first interface comprises a plurality of electrodes arranged on a substrate formed of an insulating material; and
    the second interface comprises a plurality of electrodes alternately arranged with the electrodes of the first interface on the substrate so that each of the electrodes of the second interface is disposed within a critical distance from at least one of the electrodes of the first interface.

5. The bioelectric signal measurement apparatus of claim 1, wherein the first interface comprises a single electrode; and the second interface comprises a plurality of electrodes surrounding the single electrode of the first interface so that each of the electrodes of the second interface is disposed within a critical distance from the single electrode of the first interface.

6. The bioelectric signal measurement apparatus of claim 1, wherein the first interface comprises at least one wet electrode; and the second interface comprises at least one dry electrode.

7. The bioelectric signal measurement apparatus of claim 1, wherein the signal processor comprises:

a motion artifact extraction unit configured to extract a signal proportional to the motion artifact using the motion artifact signal detected by the second interface; and a bioelectric signal extraction unit configured to remove the motion artifact from the detected bioelectric signal using the signal proportional to the motion artifact.

8. The bioelectric signal measurement apparatus of claim 7, further comprising:

a third interface including at least one electrode configured to detect the bioelectric signal through electrical interfacing with the skin, the third interface being separated from the first interface by a predetermined distance; and a fourth interface including at least one electrode configured to detect only the motion artifact signal different from the bioelectric signal through electrical interfacing with the skin, the at least one electrode included in the fourth interface electrically interfacing with the skin in the state that is different from the state in which the at least one electrode included in the first interface electrically interfaces with the skin;

wherein the second interface is disposed within a critical distance from the first interface;

the fourth interface is disposed within the critical distance from the third interface;

the signal detected by the second interface and the fourth interface is an electric potential signal; and the motion artifact extraction unit is further configured to extract the signal proportional to the motion artifact by differentially amplifying electric potential values of the electric potential signal detected by the second interface and the fourth interface.

9. The bioelectric signal measurement apparatus of claim 8, wherein the motion artifact extraction unit is further configured to:

apply a predetermined current modulated at a predetermined frequency to the skin through the second interface and the fourth interface to produce the electric potential values of the electric potential signal;

differentially amplify the electric potential values of the electric potential signal to produce an amplified signal; and demodulate the amplified signal to extract the signal proportional to the motion artifact.

10. The bioelectric signal measurement apparatus of claim 8, wherein the bioelectric signal extraction unit is further configured to:

extract a bioelectric signal including the motion artifact by differentially amplifying electric potential values of the bioelectric signal detected by the first interface and the third interface; and remove the signal proportional to the motion artifact from the bioelectric signal including the motion artifact to obtain a bioelectric signal free of the motion artifact.

11. The bioelectric signal measurement apparatus of claim 7, wherein the bioelectric signal extraction unit is further configured to:

adaptively filter the signal proportional to the motion artifact to obtain an estimated motion artifact signal; and remove the estimated motion artifact signal from the detected bioelectric signal to obtain a bioelectric signal free of the motion artifact.

12. The bioelectric signal measurement apparatus of claim 1, wherein the first interface and the second interface are disposed to be separated from each other.

13. A bioelectric signal measurement apparatus, comprising:

a first interface including at least one electrode configured to detect a first signal from a skin of a testee, the detected first signal detected by the first interface being distorted by movement between the first interface and the skin;

a second interface including at least one electrode configured to detect a second signal from the skin, the detected second signal detected by the second interface being only a motion artifact signal distorted by movement between the second interface and the skin, the at least one electrode included in the second interface electrically interfacing with the skin in a state that is different from a state in which the at least one electrode in the first interface electrically interfaces with the skin, and a distortion of the detected second signal detected by the second interface being greater than a distortion of the detected first signal detected by the first interface; and a signal processor configured to obtain a signal free of distortion due to the movement between the first interface and the skin from the detected first signal detected by the first interface using the detected second signal detected by the second interface.

14. The bioelectric signal measurement apparatus of claim 13, wherein a contact impedance between the second interface and the skin is larger than a contact impedance between the first interface and the skin, causing the distortion of the detected second signal detected by the second interface to be greater than the distortion of the detected first signal detected by the first interface.

15. The bioelectric signal measurement apparatus of claim 13, wherein the at least one electrode included in the first interface comprises a sharp protrusion configured to penetrate a stratum corneum of the skin; and the at least one electrode included in the second interface comprises a flat plate configured to contact a surface of the skin.

16. The bioelectric signal measurement apparatus of claim 13, wherein the second interface is disposed within a critical distance from the first interface so that the distortion of the detected second signal detected by the second interface has substantially a same shape as the distortion of the detected first signal detected by the first interface.

17. The bioelectric signal measurement apparatus of claim 13, wherein the first interface and the second interface are disposed to be separated from each other.

\* \* \* \* \*